US007229637B2

(12) United States Patent
Zenovich et al.

(10) Patent No.: US 7,229,637 B2
(45) Date of Patent: Jun. 12, 2007

(54) PHYSIOLOGICALLY ACTIVE AGENTS CONTAINING VICINAL DITHIOGLYCOLS AND USE THEREOF IN VARIOUS BRANCHES OF ECONOMY

(76) Inventors: Sergei Mikhailovich Zenovich, ploschad Pobedy, 2, korp. 2, kv.206, Russian Federation, 121170, Moscow (RU); Boris Khaimovich Strelets, prospekt Nauki 6, korn, 1, kv, 43, Russian Federation, 195113, St. Petersburg (RU)

( * ) Notice: Subject to any disclaimer, the term of this patent is extended or adjusted under 35 U.S.C. 154(b) by 378 days.

(21) Appl. No.: 10/169,367

(22) PCT Filed: Dec. 28, 2000

(86) PCT No.: PCT/RU00/00535

§ 371 (c)(1),
(2), (4) Date: Jul. 1, 2002

(87) PCT Pub. No.: WO01/49822

PCT Pub. Date: Jul. 12, 2001

(65) Prior Publication Data

US 2003/0018063 A1    Jan. 23, 2003

(30) Foreign Application Priority Data

Dec. 29, 1999 (RU) ................. 99127022
Feb. 25, 2000 (RU) ................. 2000104533

(51) Int. Cl.
*A61K 47/00* (2006.01)
*A61K 9/70* (2006.01)
*A23K 1/17* (2006.01)
*A61K 9/20* (2006.01)

(52) U.S. Cl. .............. 424/439; 424/442; 424/449; 424/464; 424/70.1

(58) Field of Classification Search ............... 514/440, 514/553, 557; 424/449, 70.1, 439, 442, 464
See application file for complete search history.

(56) References Cited

U.S. PATENT DOCUMENTS 4,220,660 A * 9/1980 Brock
6,077,838 A * 6/2000 Hausheer

FOREIGN PATENT DOCUMENTS

| RU | 2067398 | 3/1991 |
|---|---|---|
| RU | 2005391 | 1/1994 |
| RU | 2013965 | 6/1994 |
| RU | 2019980 | 9/1994 |
| RU | 2035911 | 5/1995 |
| RU | 2044543 | 9/1995 |
| RU | 2059407 | 5/1996 |
| RU | 2061311 | 5/1996 |
| RU | 95103431 | 12/1996 |
| RU | 2086163 | 8/1997 |
| RU | 2095009 | 11/1997 |
| RU | 2099984 | 12/1997 |
| RU | 2104297 | 2/1998 |
| RU | 2109460 | 4/1998 |
| RU | 95117559 | 4/1998 |
| RU | 2113216 | 6/1998 |
| RU | 2127576 | 3/1999 |
| RU | 2129156 | 4/1999 |
| RU | 2131680 | 6/1999 |
| RU | 2134045 | 8/1999 |
| RU | 2137402 | 9/1999 |
| RU | 2141307 | 11/1999 |
| RU | 2141763 | 11/1999 |
| RU | 2145841 | 2/2000 |
| RU | 2145845 | 2/2000 |

OTHER PUBLICATIONS

Mashkovsky, M.D., "Medicaments: Manual on pharmacotherapy for physicians" Moscow *Meditsina*, vol. 2, pp. 181-182, (1984).
English translation of the claims RU 2044543 published Sep. 27, 1995.
English translation of the claims RU 2137402 published Sep. 20, 1999.
English translation of the claims RU 2067398 published Mar. 28, 1991.
English translation of the claims RU 2109460 published Apr. 27, 1998.
English translation of the claims RU 2019980 published Sep. 30, 1994.
English translation of the claims RU 95103431 published Dec. 10, 1996.
English translation of the claims RU 2129156 published Apr. 20, 1999.
English translation of the claims RU 2005391 published Jan. 15, 1994.
English translation of the claims RU 2131680 published Jun. 20, 1999.
English translation of the claims RU 2061311 published May 27, 1996.

(Continued)

*Primary Examiner*—Humera N Sheikh
(74) *Attorney, Agent, or Firm*—Ladas and Parry LLP

(57) ABSTRACT

The invention relates to the food and medical industries, medical cosmetics, dermatology, agriculture and the mixed feed industry. According to the invention vicinal dithioglycole (common formula $RCH(SH)CH(SH)R^{-1}$ (I)) is used as a food additive, a food product, physiologically-active substances and active ingredients of forage additives and of forage, in cosmetic and/or dermatological and skin-therapeutic remedies. The invention comprises methods for producing such additives, products and remedies. The substance of formula (I) stimulates physiological processes, increases human and animal immunity, inhibits undesirable process in organisms and food products, produces curative and preventive action of skin, hair and nails and after vicinal dithioglycole is administered the intoxication effect of alcohol consumption known as hang-over is completely remored.

11 Claims, No Drawings

OTHER PUBLICATIONS

English translation of the claims RU 2086163 published Aug. 10, 1997.
English translation of the claims RU 95117559 published Apr. 27, 1998.
English translation of the claims RU 2095009 published Nov. 10, 1997.
English translation of the claims RU 2141763 published Nov. 27, 1999.
English translation of the claims RU 2013965 dated Jun. 15, 1994.
English translation of the claims RU 2035911 dated May 27, 1995.
English translation of the claims RU 2059407 dated May 10, 1996.
English translation of the claims RU 2099984 dated Dec. 27, 1997.
English translation of the claims RU 2104297 dated Feb. 10, 1998.
English translation of the claims RU 2113216 dated Jun. 20, 1998.
English translation of the claims RU 2127579 dated Mar. 20, 1999.
English translation of the claims RU 2134045 dated Aug. 10, 1999.
English translation of the claims RU 2141307 dated Nov. 20, 1999.
English translation of the claims RU 2145841 dated Feb. 27, 2000.
English translation of the claims RU 2145845 dated Feb. 27, 2000.
*Chemical Encyclopedia,* Moscow, Sovietskaya Encyclopedia publishers (1990), vol. 2, pp. 91-92.
Catalogue *Journal of Cosmetics Market of Russia* (1998) No. 3.
V.F. Dobrovolsky "Home and Foreign Experience in Creating Products of Prophylactic Action." The Research Institute of the Food-concentrates Industry and Special Food Technology (1998) pp. 54-55.

* cited by examiner

PHYSIOLOGICALLY ACTIVE AGENTS CONTAINING VICINAL DITHIOGLYCOLS AND USE THEREOF IN VARIOUS BRANCHES OF ECONOMY

FIELD OF THE INVENTION

Food Production

The invention relates to the production of food and it may be used to obtain a food additive which extends the shelf life of food products and a food supplement which is able to improve the immunity and to provide a physiologically beneficial effect; the supplement may be widely used for alleviating the hangover syndrome and which may be added into liquors and soft drinks, into bakery products, confectionery and other food.

Cosmetology and Dermatology

The invention also relates to cosmetics, in particular to medical cosmetics and dermatology and may be used to obtain novel cosmetic agents comprising, as active ingredients having cosmetic dermatological action, vicinal dithioglycols which have physiologically beneficial properties allowing to provide novel characteristics of cosmetic means for the treatment of skin and hair. The invention relates to a novel topical formulation, to a method for using the formulation and to a method for producing the same. It relates to compositions able to improve the condition and appearance of skin and to provide therapeutic, therapeutic-prophylactic effect on the skin and which are able to beneficially act on hair.

Animal and Poultry Keeping

The invention also relates to agriculture and may be us-ed, for instance, for production of feed and mixed fodder, or in veterinary, when physiologically active substances and active ingredients are administered to agricultural animals, pets and poultry, with feed additives to enhance the immunity, to promote growth and important physiological processes in the organisms of the animals and poultry, to reduce the level of heavy metals and toxic compounds in milk of the dairy cattle and in meat of the livestock and poultry.

BACKGROUND OF THE INVENTION

Food Production

RU patent 2134045 C1 (published on Aug. 10, 1999) discloses a food supplement comprising a base and Eleuterococcus extract, as well as a method for producing the supplement, comprising the steps of mixing ingredients, pelleting and drying.

RU patent 2,131,680 C1 (1999) suggests to use lactulose as an additive to soft drinks to alleviate the hangover syndrome to provide a protecting effect on the liver. Lactulose may be added in dry or liquid form to soft drinks in a technologically acceptable amount. First, the advantageous effect of lactulose is based on that it binds and brings out from the body some toxic substances present in the consumed liquor, and second, it diminishes the stress effected on liver by ammonia and amines, by means of promoting the growth of anaerobic lactobacteria in large intestine.

RU 2005391 C1 (1994) discloses a soft drink "Ametist" for elimination of harmful effects of consumption of beverage alcohol, such as ethanol withdrawal syndrome and damaging effect of post-intoxication on the heart. The drink is prepared by adding choline and glycerol to water, mineral water or fruit or vegetable juice used as a liquid base, this base being a source of potassium and sodium salts and fructose. Said additives are added to the product in appropriate amounts.

RU 2129156 C1 (1999) discloses a method for preparing vodka, comprising adding 10–50 $mg/dim^3$ of succinic acid sodium salt thereof (sodium succinate) to preliminary mixture of water and ethanol after the charcoal treatment, to reduce toxic effect of ethanol and to improve quality and biological acceptability of vodka. The addition of said substances results in esterification of ethyl alcohol with the acid residue of succinic acid (succinate ion). In this reaction some esters (ethyl succinate, diethyl succinate) are formed, which have deodorizing properties; the resulting vodka has a soft smooth taste without the strong smell of ethyl alcohol. Furthermore, succinic acid is an antioxidant and prevents the formation of acetaldehydes from ethanol, thus reducing the harmful effect of vodka.

However the above mentioned ingredients, additives and supplements used the methods for preparation of beverages for alleviating the hangover syndrome demonstrate low chemical activity against the formation of stable water-soluble aldehydes and ketones which are responsible for the hangover. In addition, the prior art additives to alcohol-containing beverages to alleviate the hangover, such as fumaric or glutamic acids, do not react with aldehydes and ketones which impair quality and biological acceptability of liquors.

RU 2044543 C1 (1996) discloses the use of unithiol (a compound relating to vicinal dithioglycols) in clinical practice as an antioxidant in a complex with α-tocopherol and ascorbic acid for treatment of enteric fever (typhoid).

Cosmetology and Dermatology

Skin is a complicated multi-component system comprising different tissue layers, glands, follicules and other systems providing intracellular and extracellular flows. Therefore, only the means which take into account the complexity and specific characteristics of this system may be efficiently used for skin care. Skin and hair often lose some biologically active substances because of the contact with coloring agents, cleaning agents and other chemicals, owing to non-balanced nutrition of skin, hair or of the whole body. Said and other factors lead to disbalance of metabolic processes. The skin care is often connected with the treatment of skin exposed to a harmful external influence of heat, radiation or other deleterious conditions.

RU 2145841 C1 (2000) discloses a method for improving therapeutic properties of vegetable preparations for care of the head skin and hair, comprising adding ceolite particles having a size distribution from 0.01 to 10 μm in amount of 30 to 50 wt. % to the vegetable preparation after drying and grinding the vegetable starting material into powder. Advantageous dermatological properties of the vegetable preparation obtained by the method are connected with the surface absorption of ceolite particles, enhancing the ability of alkaloid molecules to act on the hair and skin of the head, and this leads to enhancing the therapeutic effect of medicinal herbs for treating skin disorders. The method is directed to the enhancement of the effect of biologically active substances present in traditional vegetable components of cosmetic products. Although the added ceolite comprises useful microelements, it does not comprise substances promoting the transference of the microelements deep into the skin tissue; the lack of said substances to some extent reduces the therapeutic effect of the preparation obtained by the method.

RU 2113216 C1 (1998) discloses a cosmetic formulation accelerating the renewal of the skin cells at a small irritation;

the formulation comprises a mixture of organic acids derivatives thereof taken in a certain proportion, an anti-irritation agent, antioxidants other substances traditionally applied in cosmetics and dermatology. In preferred embodiments, keratolytic agents are used, which do not cause excessive immune response. However the disclosed formulation does not comprise the substances for replenishing sulfhydryl groups of sulfur-containing amino acids which are indispensable for promotion of the growth of keratin-containing tissues.

RU 2127579 C1 (1999) discloses a preparation for care of the head skin, said means comprises a lipid base, a preservative, a fragrant, cysteine, $\alpha$-tocopherol, emulsified liquid glycerides of subcutaneous fat of a sea mammal as a lipid base, and methyl ester of paraoxybenzoic acid at a certain quantitative ratio of components being used as a preservative (the patent. The drawback of the known agent consists in that the added sulfur-containing amino acid cysteine being a valuable additive, does not provide for penetration of metal ions into cells of the skin tissues as well as does not provide for a complex antioxidant and preserving effects on the composition of the cosmetic formulation.

Active ingredients of the mentioned cosmetic preparations and methods consist have insufficient chemical activity for binding and removing toxins or toxic metal compounds, therefore they are accumulated in the skin, effecting further damage to the skin. Furthermore, the above indicated agents and methods do not offer the combination of high physiological activity, antioxidant properties and stimulating effect, along with the binding and elimination of toxins.

Animal and Poultry Keeping

The prior art agents useful as feed additives in breeding cattle, poultry and furry animals for various aims including reduction of undesirable and toxic substances in the products of animal origin, intensification of growth of animals and poultry, improving the quality of fur, etc. are known.

For example, RU 2013965 discloses an absorbent additive which is a by-product obtained during clarification of wine. The additive comprises transition metal ferrocyanide and bentonite to reduce the level of radionuclides in the flesh of the animal by preventing transfer of cesium radionuclides from the feed into the body of the animal.

RU 2035911 C1 (1995) discloses a method for promoting the growth of broilers, comprising the administration of a supplement in the form of a concentrated vegetable extract from lucerne (alfalfa) hay, the extract comprising water-soluble salts of metals such as Mo, Ba, Pb, Co, V, Cr, Zn, Fe, Sn in certain amounts per kilogram of vegetable weight.

RU 2109460 C1 (1998) discloses a granulated composition for feeding ruminant animals and a method for producing the same. The granules include a coating layer and a core comprising a physiologically active agent. In said composition the physiologically active agent is at least one substance selected from the group consisting of amino acids, amino acid derivatives, vitamins, vitamin derivatives, enzymes, medicaments for animals, hormones, carbohydrates, nutrients, microorganisms, minerals and mixtures thereof.

RU 2019980 C1 (1994) discloses a composition for improving the quality of fur obtained from furry animals. It comprises a carrier and a mixture of amino acids, and it is subcutaneously administered to the animal.

RU 2145845 C1 (1995) discloses a supplement comprising ionophore, selenium, suitable veterinary medicaments, a carrier, diluent, filler adjuvant. The supplement is administered to animals in capsules for prolonged release and increases the weight gain of the animals, prevents diseases of the animals owing to the increased consumption of the active ingredients of the supplement.

RU 2067398 C1 (1996) discloses a feed additive and a method for feeding turkey, wherein the novel use is made of the known synthetic 4,9,11-triene steroids, in particular, trenbolone acetate, as a feed additive for oral administration instead of their subcutaneous administration used previously.

However the above additives and active agents have insufficient chemical activity to bind and remove various toxins or toxic metal compounds from the body, and this leads to accumulation of the harmftil substances in animals and in food obtained from them. Furthermore, the above agents and methods do not provide high physiological activity, antioxidant properties and the strengthening of immunity, in addition to the binding and eliminating of toxic substances, the intoxication effect of alcohol consumption.

The U.S. Pat. No. 4,594,249 discloses a method of altering the intoxicating effects of beverage alcohol. In the immediate short term, it reduces the effects of intoxication from the consumption of more than moderate quantities of alcohol by reducing symptoms such as slurred speech, blood alcohol levels. In the longer short term, it reduces or eliminates the next day effects of alcohol consumption known as hang-over. In the long run, the method eliminates or reduces the long term effects of heavy consumption of alcohol: depression, delirium tremens, peptic ulcers, cirrhosis of the liver, fetus damage, pancreatitis, alcohol related death, and associated alcohol related disabilities.

The method is based in the consumption by the subject of Sob'r-K™ before, during and/or following consumption of alcohol.

SUMMARY OF THE INVENTION

Food Production

The present invention uses vicinal dithioglycols as a food additive or supplement. Said dithioglycols strengthen the immunity and stimulate essential physiologic processes such as glycolysis, metabolism of lipids and metal ions, and enzymatic processes. They may bind various radicals and inhibit undesirable processes in the body and in food, such as peroxidation of fatty acids. It is found that the beneficial effect of vicinal dithioglycols, in addition to their known properties, is connected with their ability of the physiologically irreversible binding of carbonyl compounds present in food and in the body, including the binding of ketone bodies formed in the body, as well as with their ability to form complexes with bivalent metal ions, providing the physiologically beneficial effect on transportation of said ions through the membranes of cells, on glycolysis, on enzymatic catalysis, on catabolism of amino acids molecules and on thiol-disulfide balance in the metabolism of amino acids. In addition to the above stated advantageous effects, the use of vicinal dithioglycols in food products allows to extend their shelf life, to create new healthy products, to develop novel dietary products, to add to their nutritional value and to enhance the physiological activity of the food products, to offer more food additives and supplements for consumers.

The objects of the invention are achieved by means of the use, in a food additive or supplement for novel food products, of vicinal dithioglycols having general formula (I):

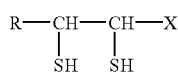

(I)

wherein R is —H, —COOH, or —SO₃H, and
X is —H, —COOH, —OH, —CH₂—COOH, —CH₂—SO₃H, or —CH₂—O—CH₂—SO₃H;
or acceptable salts of the dithioglycols having groups —OH, COOH, or —SO₃H, which are able to form a salt.

According to the present invention, a composition of the additive or supplement is provided, which comprises vicinal dithioglycol and a carrier in amount of up to 99.9999 wt. % of the total weight of the composition.

In another aspect, the present invention relates to a method for producing a food additive or supplement, the method comprises mixing vicinal dithioglycol and a carrier; the carrier being used in amount of up to 99.9999 wt. % of the total weight the composition.

In the present invention various carriers or fillers may be useful, such as flavors, fragrances, coloring agents, biologically active ingredients, mineral substances and salts thereof, vitamins, enzymes, preservatives, emulsifiers, stabilizers, pH buffering agents, antioxidants, vegetable extracts, products of animal origin, sea products, extracts from the products of animal origin or sea products, animal and vegetable proteins or protein extracts, amino acids, carbohydrates, lipids, alcohols, oils, water, soda water or mineral water of any ionic composition, organic acids, organic materials such as products of metabolism of microorganisms, products of biosynthesis, products of photosynthesis, microbial biomes or extract of the biomass produced by any known method, food additives or other ingredients appropriate for food application, or any combination of the above substances taken in the desired proportion and produced by any known physical or chemical method of treatment, maintaining or not maintaining or enhancing their biological activity.

In its further aspect, the present invention provides a food product comprising mixing a food base with vicinal dithioglycol, or with the food additive or supplement comprising vicinal dithioglycol, in a ratio in weight percents:

| | |
|---|---|
| vicinal dithioglycol, or a food additive or supplement comprising vicinal dithioglycol | 0.0001–49 |
| food base | the rest |

The advantageous result in the above aspects relating to the product and method may be achieved with any appropriate food base.

A food base of the food product may further comprise other additives such as flavoring agents, fragrances, coloring agents, biologically active ingredients, minerals or their salts, vitamins, enzymes, preservatives, emulsifiers, stabilizers, pH buffering agents, antioxidants, vegetable extracts, products of animal origin, sea products, extracts of the animal products or sea products, animal proteins, vegetable proteins, extracts of animal and vegetable proteins, amino acids, carbohydrates, lipids, alcohols, oils, water, potable mineral water having any ionic composition, organic acids, organic substances such as metabolic products of microorganisms, products of biosynthesis, products of photosynthesis, microbial biomass, extract of the microbial biomass produced by any known method, traditional food additives or ingredients, or any mixture thereof.

A food base of a product may be a beverage. Advantageously, the product will be an alcoholic drink or a soft drink or a mixture thereof.

The alcoholic drink according to the present invention will comprise a mixture of water and ethyl alcohol in any proportion (i.e. aqueous ethanol solution).

The product may be any alcoholic drink, but advantageously it will be vodka, liqueur, e.g. liqueur having fruit flavor, schnapps, cognac, brandy, whisky, gin, rum, calvados, sake, tequila or any other liquor, wine, vermouth, champagne or any other effervescent wine, beer or an alcoholic drink having a lower content of alcohol.

Soft drink according to the present invention may comprise potable water taken in a liquid state or solid state (in the form of ice), including mineral water having any composition, fruit juice, vegetable juice, or any mixture thereof in any combinations and proportions; the soft drink may comprise milk or milk products, tea, coffee, cacao, kissel, compote or fruit drink.

The food base for the food product may be confectionery or a semi-finished product.

The confectionery according to the invention may be advantageously caramel, marmalade, chewable marmalade, expanded (whipped) confectionery comprising texturing agents, baked confectionery, chewing gum, ice cream, or chocolate confectionery.

The food base for the confectionery product may comprise sugar, salt, substitutes thereof, or dry beverage mix.

The food base may be an extruded food product. Suitable extruded food products include the products of processing cereals or potato.

The food base may be tinned product including such products as vegetables, meat, fish, fruit and berries.

Tinned fruit is advantageously olives.

The baked food base may be advantageously crackers, rolls or shortbread.

Dried fruit, candied fruit, nuts and seeds are also suitable as the food base according to the present invention.

Another aspect of the invention relates to the method for producing a food product, comprising adding vicinal dithioglycol or a food additive or supplement comprising vicinal dithioglycol, to a food base in the process of preparing the food product, wherein vicinal dithioglycol or an additive comprising vicinal dithioglycol is taken in amount from 0.0001 to 49 wt. % of the total weight of the food product.

The food base, vicinal dithioglycol, food additive or supplement comprising at least one vicinal dithioglycol, taken in any physical or chemical state, may be subjected to a chemical treatment which may include such reaction as addition, splitting, oxidation, reduction, to a mechanical treatment which may advantageously include mixing, grinding, separation, vibration treatment, isolation, dilution, filtration, degassing, vacuum blowing, carbonation or saturation with a mixture of gases, concentration advantageously using the methods of membrane separation or methods of sorption; they may be subjected to thermal, electromagnetic, electrophysical, bioenergetic, acoustic, ultrasound treatment or aggregation. At the same time, the addition of vicinal dithioglycol to the food base or food additive/supplement comprising vicinal dithioglycol may be carried out by means of soaking, adhesion, dispersing a solution comprising at least one vicinal dithioglycol, spraying at least one dry vicinal dithioglycol or a dry mixture comprising it on the food base. The product may be subjected to finishing treatment, advantageously such as aggregation, granulation, tabletting, cooling, heating, pasteurization, sterilization, prepackaging or packaging.

The advantageous result may be achieved by adding vicinal dithioglycol or a food additive/supplement comprising thereof, to any food base.

As the food base may be used such products as flavors, fragrances, coloring agents, biologically active ingredients, mineral substances and salts thereof, vitamins, enzymes, preservatives, emulsifiers, stabilizers, pH buffering agents, antioxidants, vegetable extracts, products of animal origin, sea products, extracts from the products of animal origin or sea products, animal and vegetable proteins or protein extracts, amino acids, carbohydrates, lipids, alcohols, oils, water, soda water or mineral water of any ionic composition, organic acids, organic materials such as products of metabolism of microorganisms, products of biosynthesis, products of photosynthesis, microbial biomass or extract of the biomass produced by any known method, food additives or other ingredients appropriate for food application, or any combination of the above substances taken in the desired proportion and produced by any known physical or chemical method of treatment, maintaining or not maintaining or enhancing their biological activity.

Any beverage may be used as a food base for preparing the food product according to the present invention.

An alcoholic drink or a soft drink or a mixture thereof may be advantageously used as the beverage.

The addition of at least one vicinal dithioglycol to an alcoholic drink provides further effect consisting in imparting soft smooth flavor and taste to the alcoholic drink, free from the strong smell of booze. Such effect is explained by chemical interaction of vicinal dithioglycol with aldehydes present in the alcoholic drink, binding the aldehydes, which improves the sensory characteristics of the beverage according to the present invention.

In this case an alcoholic drink may be prepared by a simple mixing drinking water and ethyl alcohol.

As an alcoholic drink, use may be advantageously made of ready made vodka, different liqueurs, including fruit liqueur, schnapps, cognac, brandy, whisky, gin, rum, calvados, sake, tequila, any other liquor, wine, vermouth, champagne, other effervescent wine, beer, other beverages having lower content of ethanol or semi-finished beverages of this group.

Soft drink according to the present invention may comprise potable water taken in a liquid state or solid state (in the form of ice), including mineral water having any composition, fruit juice, vegetable juice, or any mixture thereof in any combinations and proportions; the soft drink may comprise milk or milk products, tea, coffee, cacao, kissel, compote or fruit drink.

The food base for the food product may be confectionery or a semi-finished product.

The confectionery according to the invention may be advantageously caramel, marmalade, chewable marmalade, expanded (whipped) confectionery comprising texturing agents, baked confectionery, chewing gum, ice cream, or chocolate confectionery.

The food base for the confectionery product may comprise sugar, salt, substitutes thereof, or dry beverage mix.

The food base may be an extruded food product. Suitable extruded food products include the products of processing cereals or potato.

The food base may be tinned product including such products as vegetables, meat, fish, fruit and berries.

Tinned fruit is advantageously olives.

The baked food base may be advantageously crackers, rolls or shortbread.

Dried fruit, candied fruit, nuts and seeds are also suitable as the food base according to the present invention.

If a food product having biologically active properties is required, vicinal dithioglycol may be added to any food product from the above group, imparting immunity correction and other physiologically useful properties to the final product. The amount of vicinal dithioglycol added one way or another the to food products depends on its specific application. When it is used as preservative for a tinned product, the added amount of dithioglycol is selected with regard to the composition and properties of the tinned product and to the required period of storage. When vicinal dithioglycol is used to impart biologically active properties to the food product, then its amount is selected with regard to physiological requirements and economic considerations.

The food additive comprising vicinal dithioglycol has the property of extending shelf life (the period of storage) of the food products, as well as of improving their quality, owing to reduction of oxidative processes and the physiologically irreversible binding of carbonyl compounds present of formed in the food products. The food supplement comprising vicinal dithioglycol has immunity correction properties too, owing to its effective physiologically irreversible binding of carbonyl compounds which are present both in food and body, and owing to the binding of ketone bodies in the human body in the following reaction (2):

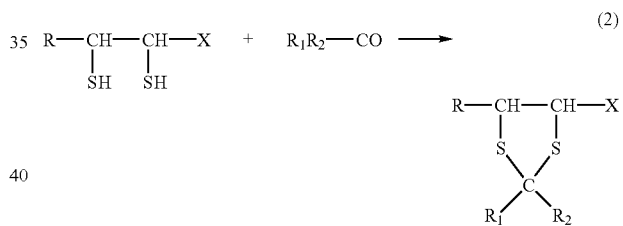

wherein $R_1$ and $R_2$ are any carbohydrate radicals or hydrogen, the reaction products being stable, water soluble and easily removable from the body. Furthermore, the effect of vicinal dithioglycols on the immune system and other systems of the human body is achieved by their ability to stimulate physiologically beneficial processes in the body and to inhibit undesirable processes. Accomplished studies have shown that vicinal dithioglycols, in addition to the immunity correction (or immunity modification), also demonstrate immunostimulating effect, subject to the method of application, its specific target and state of health.

The advantageous result is achieved owing to prompt and physiologically irreversible interaction between vicinal dithioglycol and carbonyl compounds present both in food products and in the human body, owing to the binding of ketone bodies in the reaction (2) resulting in formation of cyclic thioacetal or ketal which are easily eliminated from the human body, as well as owing to the effect on the thiol-disulfide equilibrium in metabolism of amino acids and owing to inhibition of undesirable processes such as lipid peroxidation.

In particular, vicinal dithioglycols include:

1. Dithioglycerol ("Dicaptol", BAL) of formula (6):

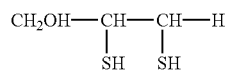  (6)

2. Sodium 2,3-Dimercaptopropane sulfonate ("Unithiol") having formula (7):

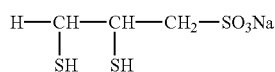  (7)

3. 2,3-Dimercaptosuccinic acid ("Succimer") of formula (8):

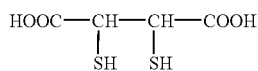  (8)

4. Sodium 2-(2,3-Dimercaptopropoxy)ethane sulfonate ("Oxathi-ol") having formula (9):

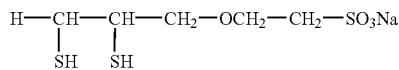  (9)

Vicinal dithioglycols are used as medicaments providing protective effect against radiation, and as antidotes in the cases of intoxication with heavy metals and their compounds, in particular, for the treatment of arsenic, lead or mercury intoxication (Mashkovsky M. D., "*Medicine preparations*", Moscow, Meditsina publishers, 1988, Vol.2, pp. 181–183; and "*Chemical Encyclopedia*", Moscow, Sovietskaya Encyclopedia publishers, 1990, Vol.2, pp. 91–92). The above compounds are water-soluble substances of low molecular weight, having two vicinal (i.e. adjacent) mercapto-groups being the active sites for capturing heavy metals, radionuclides included. The chemical properties of said compounds are well studied.

The physiologically beneficial effect of vicinal dithioglycols on the immune system and other systems of the human body may be further explained by the ability of the dithioglycols to form complexes with ions of bivalent metals, for example, calcium, magnesium, zinc, which complexes provide a beneficial effect on the processes of transportation of metal ions through the cell membranes, on glycolysis, on enzymatic catalysis, on catabolism of carbohydrate moieties of amino acids and other processes, by reaction (3) (exemplified for zinc):

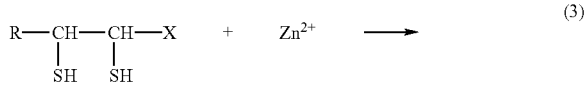  (3)

-continued

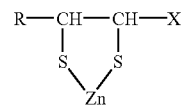

The maintenance of thiol-disulfide equilibrium in body tissues due to the presence of dithioglycol is provided owing to that, when natural amino acids are spent in the enzymatic catalysis, the deficiency in thioalcohol group (—SH) in cysteine and homocysteine is filled from dithioglycol.

Furthermore, the studies have shown that vicinal dithioglycols are able to extend the shelf life of food products. This may be explained by the chemical activity of vicinal dithioglycols in respect to peroxide radicals. The preserving effect may be also achieved by virtue of binding carbonyl compounds present in the product or formed during the storage.

Thus, the advantageous result is achieved owing to the complex effect of vicinal dithioglycols on the human body; the effect combines the immunity correction properties and chemical activity in respect to ketone bodies and carbonyl compounds, in particular aldehydes and ketones. The use of vicinal dithioglycol as a therapeutic antioxidant agent is known. Thus, in addition to the known antioxidant effect, vicinal dithioglycol also has novel properties of the binding of carbonyl compounds, stimulation of important physiological processes and inhibition of undesirable processes in the body. Such combination of properties allows to use vicinal dithioglycols, for example Unithiol, Succimer and other substances of this group, separately or in the form of mixtures, as a food additive or supplement to food products and as an ingredient of food additives and supplements. Besides, vicinal dithioglycol may be used in particular for elimination of the hangover symptoms, that is, the unpleasant consequences of alcohol consumption, appearing next day after the intake of alcohol, —headache, weakness and so on. In our opinion, the food additive comprising vicinal dithioglycol may be widely used in food and agricultural products as the preservative at the same time.

Cosmetology and Dermatology:

According to another aspect of the present invention, it is suggested to use vicinal dithioglycols for developing new cosmetic and dermatological products having improved physiological effects such as antioxidizing, stimulating and detoxicating effects on the skin, on tissues close to the skin and on hair, and stimulating other important physiological processes such as glycolysis, lipid metabolism, transportation of metal ions, enzymatic processes, the binding of undesirable radicals and inhibition of undesirable processes such as fatty acid peroxidation. The use of vicinal dithioglycols in said preparations allow to enhance their biologically active properties.

Thus, for advantageous result, it is suggested to use vicinal dithioglycols which were previously used as antidotes in case of intoxication with heavy metals, as an active ingredient of cosmetic or dermatological compositions, cosmetic or dermatological preparations, or dermatological medicaments.

The cosmetic or dermatological preparations according to the present invention, comprising at least one vicinal dithioglycol demonstrate immunity modification and antioxidant properties; it has biologically active effect on the skin tissues, on keratin materials and on the whole body; and they provide the binding and elimination of the heavy metal compounds from skin tissues and hair, as well. Vicinal dithioglycols previously have not been used as active ingredients of cosmetic or dermatological preparations or in preparation of physiologically active means for the medical treatment of the skin, keratin material, having the effect of immunity modification and stimulation, protection and antioxidizing. In addition, vicinal dithioglycols were never used in dermatology and cosmetology as active ingredients for solving the problem of elimination of heavy metal compounds from skin tissues and hair, for binding peroxide radicals in skin tissues, to reduction of irritating effect of the preparation on the skin and mucous membranes, as well as to enhance biological value and activity of cosmetic and dermatological preparations and to extend their shelf life.

The advantageous result is achieved owing to the physiologically irreversible interaction between vicinal dithioglycol and heavy metal ions, resulting in formation of complexes; said metal including Pb, Hg, and such ions as $As^{3+}$, $Sb^{3+}$, $Bi^{3+}$ which relate to the widespread man-caused toxins. The metal-dithioglycol complexes of formula (4), wherein E represents As, Sb or Bi, and complexes of formula (5), wherein M represents a metal atom, are thermally stable and water soluble;

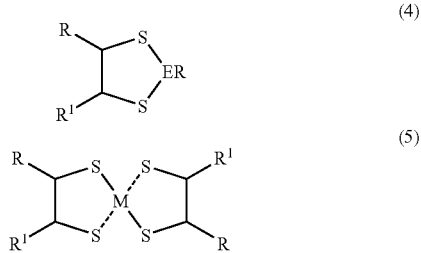

said complexes provide elimination of heavy metals from the body and regulation of thiol-disulfide equilibrium in the metabolism of amino acids, by means of binding peroxide radicals and inhibiting lipid peroxidation. Furthermore, owing to the ability of dithioglycols to form complexes with ions of calcium, magnesium, zinc and other bivalent metals, stimulating effect of vicinal dithioglycols on metabolic processes in the skin and hair tissues is achieved, providing physiologically beneficial effects on the processes of transportation of the ions through the cell membranes, on glycolysis, on enzymatic catalysis, on catabolism of carbohydrate moiety of amino acids and other processes according to the reaction (3):

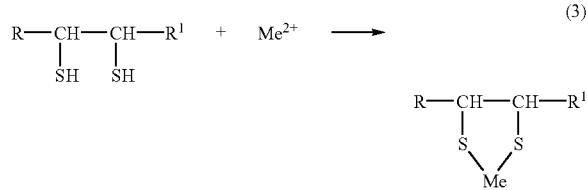

The maintenance of thiol-disulfide equilibrium in body tissues in the presence of dithioglycol is provided owing to that, when natural amino acids are spent in the enzymatic catalysis, the deficiency in thioalcohol group (—SH) in cysteine and homocysteine is filled from dithioglycol.

Taking into account that keratin comprises sulfur-containing amino acids such as cysteine and cystine, the presence of at least one vicinal dithioglycol acting as donor of sulfhydryl groups, is physiologically useful in cosmetic or dermatological compositions. In keratin molecules, the stability of disulphide bonds improves under the action of proteolytic enzymes or hydrolysis. In the presence of vicinal dithioglycol, the synthesis of keratin from amino acids intensifies, providing the stimulation of keratin growth, and in relation to pharmaceutical preparations, this action provides healing effect for the skin damaged by physical or chemical impact.

Antioxidant properties of vicinal dithioglycols may be explained by the binding of peroxide radicals, which results in the physiologically beneficial inhibition of lipid peroxidation in the skin cells. The same process of inhibiting oxidative processes in cosmetic or dermatological compositions extends their shelf life. The presence of vicinal dithioglycol in the cosmetic or dermatological compositions reduces the irritation of the skin and mucous membranes, caused by lipid degradation products such as aldehydes and ketones. Said reduction is provided owing to the ability of vicinal dithioglycols for the physiologically irreversible binding of carbonyl compounds.

Thus, the advantageous result is provided owing to the complex effect of vicinal dithioglycol, combining immunity modifying, immunity stimulating, antioxidizing properties, chemical reactivity in relation to heavy metals and metal compounds, in particular lead, tin, polonium, cadmium, antimony, arsenic, bismuth and mercury. Such combination of properties allows to use vicinal dithioglycols as active ingredients of cosmetic and dermatological preparations or compositions, and in medicaments for the skin treatment.

Thus, the advantageous result is provided by means of including at least one vicinal dithioglycol, as an active ingredient, into a cosmetic or dermatological composition, or into a medicament for the skin treatment.

Said advantageous result is achieved by that the biologically active means for treating the skin or keratin tissues, prepared in the form of a cosmetic or dermatological composition or in the form of a medicament for the skin treatment, such as ointment or dressing, comprises at least one vicinal dithioglycol as an active ingredient in the cosmetically or dermatologically acceptable carrier. Vicinal dithioglycol or a mixture of vicinal dithioglycols is used in amount of 0.00001 to 99 wt. % of the total weight of the preparation, preferably 0.0001 to 25 wt. % and more preferably 0.001 to 5 wt. %. The preparation according to the present invention further comprises at least one additive which is selected from the group consisting of thickeners, fatty acids, esters of fatty acids, glycerol esters of fatty acids, silicones, surfactants, emulsifiers, fragrances, preservatives, sun protectors, proteins, amino acids and their derivatives, organic acids and their derivatives, enzymes, hormones, vitamins and their derivatives, polymers, vegetable oils, essential oils, animal fats, mineral or synthetic oils, vegetable extracts, animal extracts, bee products, derivatives of lipids, derivatives of proteins, pickles, microelements, tannins, biologically active substances and any other additive traditionally used in the field of cosmetics and dermatology. According to one embodiment, the beneficial effect of the preparation may be enhanced by adding a salt solution comprising ions of magnesium, calcium or another bivalent metal. Vicinal dithioglycols are able to form water-soluble complexes with ions of bivalent metals; said complexes easily pass through the cell membranes, activating transportation of ions of said metals. According to another embodiment, the effectivity of the preparation may be improved by the addition of proteins to the composition of the preparation; the group of useful proteins comprises collagen, keratin or derivatives thereof, for example, their hydrolyzates. Said proteins improve the adsorbing property of the preparation, which is useful, for example, in shampoos and hair sprays. The combined action of vicinal dithioglycol and hydrolyzate of any one of the indicated proteins activates the regeneration of the skin and hair cells, compensates the deficit of amino acids, normalizes the skin hydration. The provided effect is a characteristic feature of vicinal dithioglycols, because they may be called promoters of biologically active substances. In combination with the sources of bivalent metals, vicinal dithioglycols promote the penetration of metal ions through the cell membranes; in combination with hydrolyzates of sulfur-containing proteins they activate synthesis of keratin. In other combinations vicinal dithioglycols are able to provide other physiologically beneficial effects. They will find many applications in cosmetics also owing to the fact that some of them, for example Unithiol, are water soluble antioxidants.

Advantageously, the cosmetically or dermatologically acceptable base of the preparation is water or a mixture of water and at least one cosmetically acceptable solvent. In this embodiment, water may be preliminary subjected to special treatments such as demineralization, degassing, distillation, carbonation or saturation with a mixture of gases, electrophysical treatment, electromagnetic treatment, acoustic and in particular ultrasonic treatment, membrane filtration, bioenergetic treatment. Cosmetically acceptable solvents may be selected from the group consisting of monoatomic alcohols, polyatomic alcohols, glycol ethers, esters of fatty acids and mixtures thereof.

The desired result may be achieved irrespectively of the specific form of vicinal dithioglycol present in the composition. For example, it may be diluted in a cosmetically or dermatologically acceptable carrier or it may be in the form of a dispersion of particles.

Preferably, the preparation comprising at least one vicinal dithioglycol is destined for a topical application, that is, on the skin and in particular on the skin of the head and on keratin-containing material and in particular on human hair. The preparation may be in the form of a gel, ointment, emulsion, thick cream, liniment, balsam, lotion, foam, shampoo, hair spray, or it may be in the form of a means for the hair treatment such as rinsing, coloring, discoloring (blonding), hairdressing, hair straitening, hair waving, hair fixing; it may be in the form of a means for the skin treatment such as an ointment, mask, tonic means, cleaner, spray, powder including liquid powder, compact powder, cosmetic pencil, or in any other traditional form used in the field of cosmetology or dermatology.

The desired result may be achieved irrespectively of the specific packaging of the preparation. The preparation may be packaged, for example, in a tube, small jar, or vial made of resilient and non-resilient materials, a pulverizer or an aerosol container to obtain spray or foam.

Advantageously, the preparation comprising at least one vicinal dithioglycol should be in contact with the skin or keratin-containing tissues such as hair, in order to provide the desired effect. Said contact may be accomplished for example by applying the preparation on the skin or hair. Alternatively, the contact may be accomplished by applying a material, on which the preparation according to the invention is applied. After the treatment, the applied preparation may be completely or partially removed, if it is necessary, for instance, with the use of a special hygienic sponge or by washing.

Animal and Poultry Keeping

Further aspect of the present invention relates to the novel use of vicinal dithioglycols and it is directed to the development of physiologically active agents having immunostimulating, antioxidizing and detoxicating effects on the body of animals and poultry, and which are able to stimulate other important processes such as glycolysis, metabolism of lipids, transportation of metal ions, enzymatic processes, to bind radicals as well as to inhibit undesirable processes such as peroxidation of fatty acids. The use of vicinal dithioglycols will allow to activate the beneficial properties of the feed and feed additives.

According to the present invention, it is suggested to use vicinal dithioglycols used previously as antidotes against the intoxication with heavy metals, as a physiologically active agent in the feed or feed additive for animals and poultry. Said agent has the immunostimulating and antioxidant properties; it has a biologically active effect on the animal body and it provides the binding and elimination of the heavy metal compounds from animals and poultry.

Thus, it is suggested to use vicinal dithioglycols as an active ingredient in the physiologically active composition of the feed additive or feed supplement, or in the preparations for inhalation, injection and implantation. Until recently vicinal dithioglycols were used in medicine only as antidotes or radioprotecting agents, and sometimes for different aims, but they were never used as an active ingredient for a feed supplement or as a physiologically active agent for peroral administration to animals and poultry to obtain immunostimulating and antioxidant effects. Furthermore, vicinal dithioglycols were never used in the livestock keeping as an active ingredient of feed additives for elimination of heavy metals from milk and meat products, as well as for improving dietary value and biological activity of the feed.

The advantageous result according to the present invention is achieved by physiologically irreversible interaction between vicinal dithioglycol and heavy metal ions, which form complexes including lead, mercury, $As^{3+}$, $Sb^{3+}$, $Bi^{3+}$ and other heavy metals relating to the widespread contaminants of feed and, consequently, of milk and meat. The dithioderivatives of formula (4), wherein E represents As or Sb or Bi) and complexes with metals of formula (5) (wherein M represents a metal) are thermodynamically stable and water soluble:

(4)

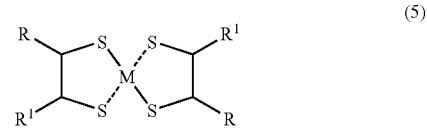

(5)

that provides for excretion thereof from the body of animals, as well as by affecting thiol-disulfide equilibrium in metabolism of amino acids, as well as by binding peroxide radicals and inhibiting peroxidation of lipids.

Furthermore, stimulating effect of vicinal dithioglycols on immune and the other systems of the animal body is achieved by the ability of said compounds to form complexes with ions of calcium, magnesium, zinc other bivalent metals; the complexes provide physiologically beneficial effects on transportation of said ions through the cell membrane, on glycolysis, enzymatic catalysis, catabolism of carbohydrate moiety of amino acids and on other physiological processes, according to the reaction (3):

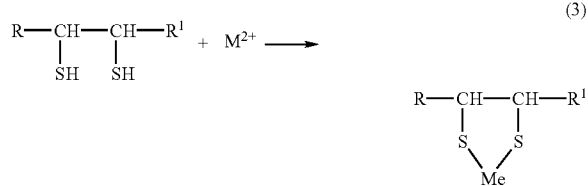

Maintenance of thiol-disulfide equilibrium in body tissues in the presence of dithioglycol is provided owing to that, when natural amino acids are spent in the enzymatic catalysis, the deficiency in thioalcohol group (—SH) in cysteine and homocysteine is filled from dithioglycol.

Antioxidant properties of vicinal dithioglycols may be explained by the binding of peroxide radicals, which results in the physiologically beneficial inhibition of lipid peroxidation in the skin cells Thus, the desired result is achieved owing to a complex action on the body of animals and poultry of the suggested chemical compound which combines in itself immunostimulating and antioxidant properties and chemically active properties in respect to heavy metals and compounds thereof, in particular to lead, tin, polonium, cadmium, antimony, arsenic, bismuth and mercury. Such a combination of properties allows using this substance as a supplement to feeds used in particular for lowering the level of heavy metals in milk and milk products as well as in meat of animals and poultry.

The advantageous result is achieved by that the physiologically active product according to the present invention comprises at least one vicinal dithioglycol and a filler or solvent in amount of up to 99.99999 wt. % of the total weight of the agent.

Advantageously, the filler or solvent suitable for the product according to the invention is a feed base, so that the proportion between vicinal dithioglycol or mixture of vicinal dithioglycols and the feed is as follows (in wt. %):

| | |
|---|---|
| vicinal dithioglycol, or a mixture of vicinal dithioglycols | 0.00001–49 |
| Feed base | the rest |

The composition of the physiologically active product may comprise the filler and/or solvent in amount of up to 99.99999 wt. % of the total weight of the means.

The product according to the invention may comprise products of animal or vegetable origin, sea products or extracts thereof, organic acids, microbial biomass, extract of the microbial biomass, products of biosynthesis, photosynthesis, chemical synthesis, pharmaceutical products, or by-products of microbiological, food or pharmaceutical industry as the feed base.

The feed base may be liquid. It may be sugar, or salt, or a dry mixture to be reconstituted with water. The feed base may also be an extruded material or semi-finished product.

A feed base may further comprise vitamins or derivatives thereof, enzymes, amino acids or derivatives thereof, hormones, minerals or salts thereof, organic acid or derivatives thereof, antioxidants, preservatives, emulsifiers, stabilizers, microorganisms, nutrients, flavors, fragrances, or coloring agents.

The content or ratio of any one of the above listed ingredients of the product according to the invention is selected with regard to the physiological reasonability, veterinary requirements and other considerations including the cost of the product.

The physiologically active product for animals and poultry may be produced in different forms. The specific form of the product is selected with regard to general and particular conditions of the animal keeping and the physiological habits of the animals and poultry to be fed with the product.

The advantageous result is also achieved by that the physiologically active product for animals and poultry may be an implant, or a mixture for inhalation, or a solution for injection.

The composition of the product may further include alcohol, oil, pH buffering agent, saline, potable water, mineral water of any composition, as a solvent for the active agent according to the present invention.

The method for producing the physiologically active product for animals and poultry comprises adding at least one vicinal dithioglycol of general formula (1) being one of the active ingredients of the product, to a filler or solvent so that the amount of vicinal dithioglycol or a mixture of vicinal dithioglycols is in the range from 0.00001 to 49 wt. % of the total weight of the product composition.

The method may include, prior to the addition of at least one vicinal dithioglycol into the filler or solvent, the step of subjecting separate ingredients or the whole composition to a chemical and/or mechanical treatment, advantageously to mixing, grinding, separation, vibration, isolation, dilution, filtration, degassing, vacuum blowing, carbonating or saturation with gas mixture, concentrating, advantageously with the membrane separation methods or sorption methods, and they may be subjected to thermal, electromagnetic, electrophysical, bioenergetic, acoustic or ultrasound treatment, or aggregation.

The addition of vicinal dithioglycol may be performed by any method, for example by surface application or soaking, by dispersing and/or spraying the solution comprising at least one vicinal dithioglycol; then the product may be subjected to a final treatment which is advantageously aggregation, granulation, tabletting, cooling, heating, and/or pasteurization, sterilization, preserving, and/or pre-packaging or packaging.

The advantageous result is also achieved by that vicinal dithioglycols of general formula (1) are used as active ingredients of feed additives.

Advantageously, the ration of animals and poultry comprises physiologically active agents, feeds or feed additives, which comprise vicinal dithioglycols of general formula (1) or which are produced by the methods comprising the step of adding vicinal dithioglycols of general formula (1).

Thus, the present invention is directed to the use of vicinal dithioglycols as active ingredients of physiologically active agents, suitable also as feed additives to the ration, as the feed ingredients, as ingredients of the preparations for injection, implantation or inhalation. The active agent for the animals and poultry provides the combination of immunostimulating, antioxidant properties and chemical activity to heavy metals and their compounds, in particular to lead, tin, polonium, cadmium, antimony, arsenic, bismuth and mercury. Said combination of properties allows to use this agent for enhancing the biological value and activity of feeds; and such feeds are recommended especially for improving the quality of fir of the furry animals, for stimulating growth and development and the other important physiological processes in the body of animals and poultry, for the reduction of the level of heavy metals and toxic compounds in milk of the dairy animals and in meat of livestock and poultry.

The Preferable Embodiments of the Present Invention

Below several examples are provided for better illustration of the present invention, but not for limitation of the invention.

EXAMPLES IN THE FIELD OF FOOD PRODUCTION

Example 1

Production of Vodka

A 40 vol. % ethanol-water mixture was prepared from rectified spirit "Extra" and potable water having hardness not more than 0.1 mg-eqv/dm$^3$ and treated on reverse osmotic apparatus. Then 0.07 kg sodium hydrocarbonate and 0.1 kg "Unithiol" were added to 10,000 liters vodka and mixed for 20–30 minutes. The resulting mixture was filtered through a coal filter at the flow rate of 30 dl/hour. After other traditional procedures the final product was bottled. The resulting vodka had soft, smooth taste and flavor; after consumption of the vodka, the hangover was milder than usual.

Example 2

Dry Beverage Mixture and a Method for Producing Thereof 700 g of sugar were ground into powder for the beverage mixture. 17 g ground salt, 17.5 g ground citric acid and 0.5 g disodium salt "Succimer", all in dry form, were added, one after another, to ⅓ of the sugar powder. Each time the mixture was thoroughly agitated. 2.6 cm$^3$ orange flavor was added to the powder mixture during continuous agitation. 260 g powder of the dry fruit of sea-buckthorn and the remaining portion (⅔) of the sugar powder were added to the flavored product. The resulting mass was divided in portions of 20 g each, and packaged. Each package was designed for obtaining 200 cm$^3$ beverage.

The prepared dry mixture had uniform orange color, sour-sweet taste and fruit odor. The beverage reconstituted from the dry mixture had an invigorating effect and provided significant alleviation of the hangover state severity.

Example 3

A Method for Producing Jelly Marmalade

To obtain jelly marmalade according to the present invention, gelatin with gel strength 180–220 g Blum was used. Gelatin was soaked in 40 kg cherry juice having 11–13 wt. % solids content, and it was left for 2–3 hours at ambient temperature (up to 25° C.) for swelling and for the formation of chelates; then gelatin is subjected to further swelling and solubilization at an elevated temperature (up to 50° C.) in a reservoir during continuous agitation. Then another reservoir having a mixer and heating jacket was filled with 25 kg sugar and 25 kg cherry juice having 11–13% solids content; the mixture was heated up to 80° C., 15 kg treacle were added and the mixture was boiled to obtain syrup having 78–79% solids content. Gelatin solution was poured into the resulting syrup at least at 70° C., and 2.2 kg citric acid and 0.01 g "Oxathiol" were added thereto. The mixture was dispensed into moulds through a dispensing device and left until hardening. The final product was packaged. Consumption of the product is recommended after the alcohol intake for alleviating the negative effects of intoxication.

Example 4

Mineral Water and a Method for Producing Thereof 0.02 kg of the mixture of "Succimer" and "Unithiol" in a weight ratio 9:1 was added introduced to 10 l of cool mineral water "Essentuki". The solution was agitated and filtered. The beverage was bottled, sealed and delivered to storage. The resulting beverage may be used as a rehabilitation means and as a means for alleviating alcohol hangover. The beverage also had beneficial physiological properties, because of the pronounced immunity correction effect.

Example 5

A Method for Producing Grape Nectar

For the production of grape nectar, 10 liters of natural grape juice were diluted with equal volume of potable water. 0.26 dm$^3$ of wine flavor was added. The mixture of 500 g sugar and 1 g "Unithiol" was added to the diluted juice. After agitation and filtering, the nectar was ready for consumption.

Example 6

A Method for Producing Sugar Drops

A syrup comprising 50 kg of treacle, 50 kg of granulated sugar and water was prepared to obtain a sugar-treacle syrup. The syrup was boiled down to 75% solids content. 1.4 kg of crystals of granulated sugar were loaded into a pelletizer and treated intermittently with sugar-treacle syrup and sugar powder, to obtain sugar particles having size of 2–3 mm. The particulate sugar was moistened with sugar syrup, and then 18.0 kg of treacle was added therein, and the particles were coated with 20 kg powder mixture comprising the peppermint fine powder and the mixture of sugar powder and "Oxanthiol" at 1:1 ratio. The mixture comprised 0.01 kg "Oxanthiol". The moistening of the particulate sugar with the sugar-treacle syrup and the coating the particulate sugar with the powder mixture were carried out until the weight of the drops increased up to 60 wt. % of the final product. Then the resulting particles were treated with sugar syrup containing 0.17 kg food dye (tatrazine) and sugar powder. The obtained semi-finished product was subjected to glossing with 0.2 kg vegetable oil comprising 0.18 kg bee wax and 1.0 kg talc. Then the drops were dried and screened to separate debris and the excess of sugar powder. The final drops had an average size of 5 mm, round shape, bright-yellow color, smooth shining surface and pleasant mint taste. The drops well dissolved in the mouth. The drops according to the present invention should to be taken after consumption of a large amount of beer or any other drink having low content of alcohol, to reduce the negative effect thereof.

Example 7

A Method for Producing Crackers in the Form of Sticks

To produce crackers in the form of sticks, dough was kneaded according to a traditional formulation, by mixing baker's yeast, salt, high grade wheat flour and water, to obtain the moisture of up to 40%. The dough was shaped in the form of sticks and baked. The solution of "Dicaptol" (supplement) in the concentration of 15 mg/l was added to the sticks by means of spraying the solution on the salt crystals and powdering the baked sticks with the treated salt. Then the sticks were packaged. Said sticks are recommended to consume as a snack to beer, to reduce the negative effect of aldehydes and ketones therein.

Example 8

A Method for Producing Biscuits

For the production of biscuits, the traditional ingredients are mixed with with the predetermined amount of water to obtain the batter emulsion. As flavors, some powder spices, for example dill, were added to the emulsion. The ingredients were used for 100 kg of flour in the following amount: 15 kg of margarine, 4.5 kg of flavor additive, 7.0 kg of sugar, 2.3 kg of salt, 0.58 kg of food soda, 4 kg of carbon-ammonium salt, 0.021 kg of citric acid, 5 kg of starch and 0.01 kg of "Unithiol". Then the mass was agitated and shaped in the form of biscuits which were baked. The biscuits are recommended for elderly people as a substitute for traditional bread; owing to dietetic properties inherent to this product, it provides a pronounced physiologically beneficial stimulating effect.

Example 9

Food Supplement and Method for Preserving Caviar of Hunchback Salmon 50 kg of hunchback salmon roes was loaded into a caviar separating device. The roes were covered with 2.5% NaCl solution and the temperature was brought up to 40° C. during agitatition; then an enzymatic agent in amount of 300 mg of the active protein per 1 kg of roes, and the agitation was continued for the next 7 minutes. Then the solution with separated pellicles was poured out, and the rinsing with 3% NaCl solution at 0° C. was effected three times. The rinsing water was removed by decantation to remove the residual pellicles and debris of the caviar. The washed caviar was put in 3% pickle comprising 2 g of the supplement according to the invention per 10 l solution. The supplement comprised NaCl, "Unithiol" and citric acid in the ratio of 1:3:1. The ready caviar was packaged in tins and stored at a temperature of from 4 to 6° C. The storage term was extended to 18 months.

Thus, the present invention is directed to the novel use of vicinal dithioglycols as food additive or supplement having biologically active properties, owing to the complex effect on the human body of vicinal dithioglycols which have the combination of immunocorrecting properties and chemical reactivity to ketone bodies and carbonyl compounds, in particular aldehydes and ketones. Said combination of properties, in addition to already known medicinal properties, allows to use said substances or mixtures as a food additive or supplement to the food products, to increase the biological value and biological activity of the food products which are recommended in particular for the alleviation of hangover symptoms.

EXAMPLES OF COSMETIC AND DERMATOLOGICAL USE

Example 1

Balm for the Head Skin Care (Balsam)

The balsam was prepared having the following composition in wt. %: about 10% of isopropyl palmitate, about 3% of concentrate of phosphatides with lecithin, about 3% of bentonite clay, about 2% of keratin hydrolyzate, about 2% of silicone wax, about 0.5% of an oil extract of α-tocopherol, about 0.5% of a fragrance, about 0.5% of 50% aqueous solution of "Succimer" disodium salt, about 0.5% of a preservative, and the rest (about 78%) is the emulsified liquid glycerides of the sea mammal subcutaneous fat. The obtained balsam provides the stimulating effect on the skin and hair. The balsam may be applied on the clean wet hair and skin of the head; it should be uniformly distributed along the hair and lightly rubbed into the skin for 2–3 minutes. After 10 minutes of the exposure, the head should be washed with warm water. The balsam makes the skin healthier, it stimulates the hair growth, resuscitates hairs and eliminates dandruff.

Example 2

Preparation for Treating a Sunburnt Skin

For the treatment of skin which was exposed to sun light (ultraviolet irradiation) for a long time, an ointment was prepared, which had the following composition (in weight %): about 2% of magnesium salt of aspartic acid, about 5% of water-alcohol solution of the extract of camomile flowers, about 1% of vitamins A, $B_1$, D, E, C, PP, about 4% of lecithin, about 1% of magnesium sulphate, about 2% of sodium lactate, about 1% of 50% ethanol solution of Unithiol, about 5% of glycerol, about 0.5% of preservative, about 3% of emulsifier, and the rest is ethanol. Owing to the presence of Unithiol which binds peroxide radicals forming in the burnt dermal layers and actively restores the water-salt balance in dermal cells by means of transportation of magnesium ion and owing to the effect of the other active components of the composition, the skin damaged with the ultra-violet irradiation is quickly recovered. The preparation according to the present invention in the form of emulsion or lotion should be applied every 3–4 hours on the exposed skin areas with a soft tampon or absorbent cotton.

EMBODIMENTS OF THE INVENTION FOR ANIMALS AND POULTRY

Example 1

It is prepared a mixture of physiologically active substances including the substances selected from the group consisting of an amino acid or derivative thereof, vitamin or derivative thereof, enzyme, medicament, hormone, carbohydrate, microorganism and mineral substance; then Succimer is added to the mixture, and the mixture is agitated; the resulting composition is coated with a protective layer and granulated. The obtained granulated composition may be used as a feed additive for ruminants; this composition allows to significantly reduce the level of lead and mercury in milk of dairy cows.

Example 2

A mixture is prepared, comprising amino acids lysine and cystine "Unithiol" and acetyl cellulose (as the filler), then the mixture is subjected to mild heating and moulding in tablets. The obtained preparation may be administered to furry animals subcutaneously, as an implant.

Example 3

For prevention of early senescence of the pet dogs and cats, an injection solution was prepared by means of adding an aqueous solution of Unithiol and other known active ingredients belonging to the group of amino acids and vitamins, to a physiological salt solution. The prepared solution was intramuscularly injected to the animals.

Example 4

Feed ration for broilers included a feed additive comprising an elevated level of heavy metals and arsenic. To reduce the level of said substances in the meat of broilers, the mixture of Succimer and Unithiol at 2:3 ratio was added to their ration for one week prior to slaughter. The mixture of vicinal dithioglycols was used in the form of an aqueous solution prepared for drinking, said solution comprised 100 mg of the dry mixture per one liter of the drinking solution.

The solution provided a positive effect; the content of mercury, cadmium, lead and zinc in the white and red meat of broilers did not exceed allowed levels.

Example 5

The experimental data have been obtained at the Chair of Stockfeeding and Feed Production of the Saint-Petersburg State Academy of Veterinary Medicine on request of the authors of the present invention.

A full-ration mixed-fodder was checked for the absence of pathogens and used for feeding broilers. Thirty 15 days broilers were divided into one control and 4 experimental groups having 6 chickens each (3 male and 3 female chickens). Poultry were kept in a four-deck pen. The conditions of feeding such as the basic ration (BR) and the addition of Unithiol according to the protocol were as follows:

Experimental group 1: BR+1.3 mg of "Unithiol" per 1 kg of the body weight;
Experimental group 2: BR+1.7 mg of "Unithiol" per 1 kg of the body weight;
Experimental group 3: BR+2.1 mg of "Unithiol" per 1 kg of the body weight;
Experimental group 4: BR+2.5 mg of "Unithiol" per 1 kg of the body weight.

Feeding was performed in accordance with experimental protocol; broilers received water ad libitum; the experiment was carried out for 42 days.

In result of the experiment, optimal amounts of "Unithiol" in the ration have been found. The presence of "Unithiol" in the ration in amount of about 1.7 mg per 1 kg of the body weight demonstrated the growth stimulating effect beginning from the 15$^{th}$ day. The average weight gain in this group was the largest, namely up to 35.8 g per day, and the gain rate was 145.9% from that in the control group. Feathering condition improvement and increased fodder consumption were noted. The level of cadmium, zinc, lead and copper in meat and liver of poultry in the experimental groups was about 1.5 times lower than that in the control group. The experimental data allow to recommend the wide application of "Unithiol" as an active ingredient of the feed additive for broilers.

Example 6

An experiment was conducted, on the inventors' initiative, on the experimental base of the All-Russia research and technological institute for aviculture (VNITIP) during which a study was given to the following tasks:
  determination of an effect produced by unithiol (DMPS) on the productivity and meat quality of broiler chickens;
  effect produced by unithiol on the accumulation of heavy metal compounds (mercury, cadmium, lead) in various tissues of poultry.

The experiment was carried out in a vivarium on broiler chickens of one cross. Poultry was grown in cell batteries from one day to six-week age. The operating parameters and feeding level met the recommendation VNITIP 1999. The experiment was conducted according to the diagram on Table I.

TABLE I

Experimental diagram

| Group No | Characteristic of group | Feeding period days from . . . to . . . | |
|---|---|---|---|
| | | Heavy metals | Unithiol |
| 1 | Basic ration (BR) | — | — |
| 2 | BR + 17 mg of unithiol For I kg of feed | — | 15–42 |
| 3 | BR + mercury 2 mg/kg + cadmium 8 mg/kg + lead 100 mg/kg/heavy metals (HM) for I kg of feed/ | 15–42 | — |
| 4 | BR + HM + 17 mg of unithiol for 1 kg of feed | 15–42 | 15–42 |
| 5 | BR + HM + 34 mg of unithiol for I kg of feed | 15–35 | 36–42 |

The poultry population: 1 and 2 groups, 35 heads each; 3,4,5 groups—6 heads each.

Indices taken into account in the experiment:

1. Chicks' individual live weight; weighing at the age of one day, 2-, 4-, 6 weeks.

2. Average daily live weight increase of the broilers over a 6-week period.

3. Safety of the poultry population, the daily record keeping of the broilers lost, with the causes of murrain established.

4. Feathering conditions, individual evaluation.

5. Feed consumption over a period of growing by way of the daily record keeping and weighing of specifies feed for each and every group, as calculated per head and per kg of live weight increase.

6. Dressed small carcass mass, individually weighing in slaughtering at the age of 6 weeks.

7. Dressed yield of meat as calculated.

8. Classification of small carcasses according to GOST 25391-82.

9. Meat qualities by way of anatomically dressing the small carcasses of broilers.

10. Chemical meat composition on terms of a dry substance.

11. Amino acid meat composition.

12. Fatty acid meat composition.

13. Contained heavy metal residual compounds (mercury, cadmium, lead) in mixed feed for the broilers.

14. Evaluation of the level of meat contamination and internal organs (liver and kidneys) of the broilers with heavy metal salts.

TABLE 2

Broiler chickens, live weight, dynamics (in grams)

| Age | Group No 1 | 2 | 3 | 4 | 5 |
|---|---|---|---|---|---|
| Daily | 42.8 | 42.9 | 42.9 | 42.8 | 42.9 |
| 2 weeks | 336.0 | 334.0 | 335.0 | 332.0 | 335.0 |
| 4 weeks | 1010.0 | 993.4 | 906.6 | 930.0 | 881.7 |
| 6 weeks | 1823.0 | 1890.5 | 1726.0 | 1880.0 | 1780.0 |

TABLE 3

Broiler chickens, average daily gain

| Age, weeks | Group No 1 | 2 | 3 | 4 | 5 |
|---|---|---|---|---|---|
| 1–2 | 20.9 | 20.8 | 20.9 | 20.7 | 20.9 |
| 2–4 | 47.9 | 47.1 | 40.8 | 42.7 | 39.1 |
| 4–6 | 59.5 | 64.1 | 58.5 | 62.1 | 64.2 |
| 1–6 | 42.3 | 44.0 | 40.1 | 41.8 | 41.4 |

TABLE 5

Broiler chickens, safety, %

| Age, weeks | Group No 1 | 2 | 3 | 4 | 5 |
|---|---|---|---|---|---|
| 2 | 100 | 100 | 100 | 100 | 100 |
| 4 | 100 | 100 | 100 | 100 | 100 |
| 6 | 97.2 | 100 | 83.3 | 100 | 83.3 |

TABLE 6

Broiler chickens, average daily gain in live weight

| Index | Group No 1 | 2 | 3 | 4 | 5 |
|---|---|---|---|---|---|
| Feed consumption per head, gr | 3730 | 3670 | 3860 | 3750 | 3780 |
| Feed consumption per kg of gain in live weight, kg | 2.09 | 1.98 | 2.29 | 2.13 | 2.17 |

TABLE 7

Broiler chickens, carcasses, meat yield, commercial qualities

| Group | Dressed carcasses, weight, gr | Meat yield, % | Inflamed sores, % | Meat category, % 1 | 2 |
|---|---|---|---|---|---|
| 1 | 1261 | 69.2 | 14.7 | 82.4 | 17.6 |
| 2 | 1310 | 69.3 | 14.2 | 88.6 | 11.4 |
| 3 | 1133 | 65.7 | — | 40.0 | 60.0 |
| 4 | 1217 | 67.6 | — | 66.7 | 33.3 |
| 5 | 1215 | 68.3 | — | 60.0 | 40.0 |

TABLE 11

Broiler chickens, chemical meat composition, %

| Index | Group No 1 | 2 | 3 | 4 | 5 |
|---|---|---|---|---|---|
| Water | 70.0 | 70.4 | 73.28 | 73.0 | 73.28 |
| Protein | 19.32 | 19.68 | 21.41 | 21.92 | 21.52 |
| Fat | 8.46 | 7.79 | 2.58 | 2.72 | 2.52 |
| Ash | 0.94 | 0.99 | 1.07 | 1.07 | 1.14 |
| Dry substance | 28.72 | 28.46 | 25.06 | 25.71 | 25.18 |

TABLE 13

Broiler chickens, fatty acid meat composition, mg per 100 gr of producta

| Name of acids | Group No 1 | 2 | 3 | 4 | 5 |
|---|---|---|---|---|---|
| Fatty acids (total) | 29.97 | 29.58 | 26.73 | 26.96 | 26.71 |
| Including: | | | | | |
| Saturated and monounsaturated | 25.15 | 22.88 | 20.91 | 20.41 | 19.99 |
| Including: | | | | | |
| Myristic | 0.20 | 0.22 | 0.21 | 0.15 | 1.29 |
| Isomyristic | 0.19 | 0.16 | 0.25 | 0.06 | 0.06 |
| Pentadecanoic | 0.15 | 0.12 | 0.28 | 0.05 | 0.07 |
| Palmitic | 7.72 | 7.05 | 6.72 | 6.13 | 5.73 |
| Stearic | 2.44 | 2.44 | 2.49 | 3.37 | 3.57 |
| Palmitoleic | 2.55 | 2.25 | 1.76 | 1.71 | 1.59 |
| Heptadecanoic | 0.80 | 0.24 | 0.35 | 0.41 | 0.14 |
| Heptadecynoic | 0.15 | 0.14 | 0.19 | 0.11 | 0.08 |
| Oleic | 10.87 | 0.13 | 8.46 | 8.39 | 7.40 |
| Isopentadecanoic | 0.08 | 0.14 | 0.20 | 0.03 | 0.06 |
| Polyunsaturated | 4.82 | 6.70 | 5.82 | 6.55 | 6.72 |
| Including: | | | | | |
| Linoleic | 4.45 | 6.41 | 5.38 | 6.30 | 6.54 |
| Linolenic | 0.37 | 0.29 | 0.44 | 0.25 | 0.18 |

TABLE 14

Heavy metal content, mg/kg

| Material investigated | MPC | Group No 1 | 2 | 3 | 4 | 5 |
|---|---|---|---|---|---|---|
| MERCURY | | | | | | |
| Liver | 0.1 | 0.061 | 0.039 | 4.37 | 2.18 | 1.12 |
| Kidneys | 0.1 | 0.085 | 0.055 | 3.50 | 2.00 | 1.05 |
| Muscular tissue | 0.02 | Not found | Not found | 1.09 | 0.375 | 0.328 |
| Mixed feed | 0.1 | 0.01 | 0.01 | 2.01 | 2.01 | 2.01 |

TABLE 14-continued

| | | Heavy metal content, mg/kg | | | | |
|---|---|---|---|---|---|---|
| Material | | Group No | | | | |
| investigated | MPC | 1 | 2 | 3 | 4 | 5 |
| CADMIUM | | | | | | |
| Liver | 0.3 | 0.057 | 0.049 | 3.90 | 2.98 | 2.30 |
| Kidneys | 0.3 | 0.103 | 0.078 | 4.96 | 3.76 | 2.97 |
| Muscular tissue | 0.03 | Not found | Not found | 0.53 | 0.37 | 0.24 |
| Mixed feed | 0.4 | 0.13 | 0.13 | 8.13 | 8.13 | 8.13 |
| LEAD | | | | | | |
| Liver | 0.6 | 0.62 | 0.40 | 6.11 | 4.80 | 3.40 |
| Kidneys | 0.6 | 0.98 | 0.67 | 10.0 | 8.50 | 7.00 |
| Muscular tissue | 0.2 | Not found | Not found | 1.44 | 0.83 | 0.54 |
| Mixed feed | 5.0 | 1.55 | 1.55 | 101.55 | 101.55 | 101.55 |
| ZINC | | | | | | |
| Liver | 100 | 118.4 | 104.1 | 104.5 | 107.2 | 104.3 |
| Kidneys | 100 | 119.1 | 95.3 | 98.8 | 103.1 | 98.2 |
| Muscular tissue | 50 | 54.4 | 50.2 | 50.7 | 50.4 | 50.3 |
| Mixed feed | 100 | 158.2 | 158.1 | 158.2 | 158.1 | 158.2 |

Conclusion

As a result of experiment it has been established:

1. The broilers of Group 2 have higher rates of growth thanks to unithiol added to ration in an amount of 17 mg/kg of feed since 2-week age.

2. The increased doses of heavy metal salts have exerted a negative influence on the safety of broiler chickens. The use of unithiol in the composition of feed additive in the $2^{nd}$ and $4^{th}$ test groups produced a favourable effect on the safety of poultry; the 100% safety of the poultry population has been obtained in these groups.

3. The lowest feed consumption for 1 kg of gain in live weight has been observed in the $2^{nd}$ group (1.98 kg) where the broilers received unithiol in ration. The use of unithiol, as an additive in feed in the $4^{th}$ and $5^{th}$ groups has likewise improved feed remuneration with products.

4. The application of unithiol made it possible to obtain the highest level of the dressed yield of meat and also good fatness.

5. The use of unithiol in the composition of feed made it possible to improve some of the indices of chemical meat composition (as to fat and dry substances), fatty acid composition (biological value as to fatty acids has been enhanced on account of an increased polyunsaturated fatty acid content in chicken meat).

6. The use of unithiol enabled one to considerably reduce a heavy metal salt content in the depositing organs and meat of the broiler chickens.

7. The meat of broiler chickens in the $2^{nd}$ group fed with unithiol additionally to feed had a highest value as to organoleptic indices, more specifically the taste and organoleptic qualities of broths.

8. The chickens of the $2^{nd}$ groups had the best value of feathering conditions.

Example 7

Experiment Description

The tests were held upon the offer's proposal. The Moscow scientific and practical Center for the drug prophylactic of the Moscow health Administration was taken as the base for it.

The experiment was schemed as follows. The participants were taken from males and females of different age groups and different alcohol intake habits. These differences were shown in the biochemical results.

The control group remained as an intact one.

The experimental group—1—took in 1 l. of a dark beer of the "Klinskoie" type every evening from the $X^{th}$ day till the $X+13^{th}$ day. That group took in the placebo every morning from the $X+1^{th}$ day till $X+7^{th}$ day, and every morning it took in from the $X+8^{th}$ day till $X+14^{th}$ day the solution of 250 mg of Unithiol in 100 g of drinking water.

The experimental group—2—took in 1 l. of a dark beer of the "Klinskoie" type every evening from the $X^{th}$ day till the $X+13^{th}$ day. That group took in the solution of 250 mg of Unithiol in 100 g of drinking water every morning from the $X+1^{th}$ day till $X+7^{th}$ day, and every morning it took in the placebo from the $X+8^{th}$ day till $X+14^{th}$ day.

The measurements of the biochemical indices were taken in the mornings in every group, and in the control groups—after 30 minutes of placebo or Unithiol intake.

When being treated with placebo the participants did not feel the relief the alleviating of the hangover symptom. The participants feld the fool hangover alleviating in 5–10 minutes after the intake of Unithiol.

The following indices of the level of the per oxidation of lipids and the condition of the liver and the brain tissues were measured:

MDA—malondialdehyde

Triglycerides

Endogenous antioxidants:

Vit. A—vitamin A

Vit. E—vitamin E

Urate—serum urate

SH-gr.—SH-groups

Aminotransferase:

ALT—alanine aminotransferase

AST—aspartate aminotransferase

In the given tables which we leave uncommented for brevity the beneficial influence for the biochemical body indices of the Unithiol intake has been impartially presented. These indices are registered during alcohol intake. Unithiol has the capacity to reduce almost to the whole extent the toxic activity of ethanol and the products of its incomplete oxidation (carbonyl compounds) to the liver and brain tissue. That observed both in the self inner sensations of the participants and in the following biochemical condition indices:

the level of lipid per oxidation, the level of endogenous antioxidants, the level of the deleterious effect for lipids and phospholipids cell and subcell components.

Control group

| Designation, sex, age | Antioxidant system (blood) | | | | | Enzymes (blood) | | Triglycerides (blood) [mmol/l] |
|---|---|---|---|---|---|---|---|---|
| | MDA (urine) [nM/ml] | Vit. A [mcg/ml] | Vit. E [mcg/ml] | Urate [$_{MK}$M] | SH-gr. [$_{MK}$M] | ALT [nmol (sec.l)] | AST [nmol (sec.l)] | |
| Initial level Start of measurements - day X. | | | | | | | | |
| A (f, 18) | 0.45 | 1.6 | 2.1 | 275 | 374 | 42 | 35 | 0.65 |
| B (f, 21) | 0.37 | 1.9 | 3.7 | 287 | 365 | 52 | 40 | 0.80 |
| C (m, 63) | 0.30 | 2.5 | 4.2 | 288 | 349 | 38 | 31 | 0.48 |
| D (f, 25) | 0.42 | 1.5 | 2.4 | 240 | 342 | 36 | 28 | 0.54 |
| E (f, 45) | 0.38 | 1.6 | 3.3 | 270 | 361 | 41 | 37 | 0.96 |
| Dynamics - 2 point Measurements - day X + 2 | | | | | | | | |
| A (f, 18) | 0.37 | | | | | | | |
| B (f, 21) | 0.40 | | | | | | | |
| C (m, 63) | 0.23 | | | | | | | |
| D (f, 25) | 0.46 | | | | | | | |
| E (f, 45) | 0.44 | | | | | | | |
| Dynamics - 3 point Measurements - day X + 4 | | | | | | | | |
| A (f, 18) | 0.41 | | | | | | | |
| B (f, 21) | 0.43 | | | | | | | |
| C (m, 63) | 0.20 | | | | | | | |
| D (f, 25) | 0.51 | | | | | | | |
| E (f, 45) | 0.45 | | | | | | | |
| Dynamics - 4 point Measurements - day X + 7 | | | | | | | | |
| A (f, 18) | 0.39 | 1.7 | 2.8 | 269 | 381 | 40 | 38 | 0.61 |
| B (f, 21) | — | 2.0 | 3.4 | 272 | 390 | 55 | 44 | 0.77 |
| C (m, 63) | 0.21 | 2.8 | 4.4 | 284 | 377 | 34 | 29 | 0.50 |
| D (f, 25) | 0.37 | 1.4 | 2.1 | 249 | 349 | 39 | 35 | 0.51 |
| E (f, 45) | 0.53 | 1.8 | 3.0 | 285 | 363 | 52 | 42 | 0.90 |
| Dynamics - 5 point Measurements - day X + 9 | | | | | | | | |
| A (f, 18) | 0.55 | | | | | | | |
| B (f, 21) | 0.42 | | | | | | | |
| C (m, 63) | 0.12 | | | | | | | |
| D (f, 25) | 0.43 | | | | | | | |
| E (f, 45) | — | | | | | | | |
| Dynamics - 6 point Measurements - day X + 11 | | | | | | | | |
| A (f, 18) | 0.44 | | | | | | | |
| B (f, 21) | 0.46 | | | | | | | |
| C (m, 63) | 0.19 | | | | | | | |
| D (f, 25) | — | | | | | | | |
| E (f, 45) | — | | | | | | | |
| Dynamics - 7 point Measurements - day X + 14 | | | | | | | | |
| A (f, 18) | 0.60 | 1.4 | 2.2 | 281 | 382 | — | — | 0.48 |
| B (f, 21) | 0.46 | 1.7 | 3.0 | 277 | 397 | 46 | 40 | 0.67 |
| C (m, 63) | 0.10 | 2.9 | 4.6 | 280 | 364 | 33 | 28 | 0.43 |
| D (f, 25) | 0.56 | 1.7 | 2.4 | 247 | 332 | 39 | 37 | 0.46 |
| E (f, 45) | — | 1.6 | 2.7 | 281 | 370 | 38 | 34 | 0.77 |

Experimental group - 1

| Designation, sex, age | Antioxidant system (blood) | | | | | Enzymes (blood) | | Triglycerides (blood) [mmol/l] |
|---|---|---|---|---|---|---|---|---|
| | MDA (urine) [nM/ml] | Vit. A [mcg/ml] | Vit. E [mcg/ml] | Urate [$_{MK}$M] | SH-gr. [$_{MK}$M] | ALT [nmol (sec.l)] | AST [nmol (sec.l)] | |
| Initial level Start of measurements - day X | | | | | | | | |
| A1 (m, 34) | 0.74 | 1.2 | 2.4 | 265 | 365 | 39 | 36 | 0.42 |
| B1 (m, 40) | 0.81 | 1.1 | 2.0 | 261 | 368 | 53 | 45 | 0.54 |
| C1 (m, 62) | 0.63 | 1.7 | 2.8 | 280 | 372 | 46 | 37 | 0.63 |
| D1 (m, 58) | 0.49 | 1.8 | 2.1 | 289 | 384 | 49 | 32 | 0.55 |

-continued

Experimental group - 1

| Designation, sex, age | Antioxidant system (blood) | | | | | Enzymes (blood) | | Triglycerides (blood) [mmoi/l] |
|---|---|---|---|---|---|---|---|---|
| | MDA (urine) [nM/ml] | Vit. A [mcg/ml] | Vit. E [mcg/ml] | Urate [$_{MK}$M] | SH-gr. [$_{MK}$M] | ALT [nmol (sec.l)] | AST [nmol (sec.l)] | |
| Dynamics - 2 point Measurements - day X + 2 | | | | | | | | |
| A1 (m, 34) | 0.84 | | | | | | | |
| B1 (m, 40) | 0.80 | | | | | | | |
| C1 (m, 62) | 0.79 | | | | | | | |
| D1 (m, 58) | 0.53 | | | | | | | |
| Dynamics - 3 point Measurements - day X + 4 | | | | | | | | |
| A1 (m, 34) | 0.95 | | | | | | | |
| B1 (m, 40) | 0.90 | | | | | | | |
| C1 (m, 62) | 1.10 | | | | | | | |
| D1 (m, 58) | 0.93 | | | | | | | |
| Dynamics - 4 point Measurements - day X + 7 | | | | | | | | |
| A1 (m, 34) | 0.93 | 0.7 | 2.0 | 210 | 354 | 93 | 90 | 0.89 |
| B1 (m, 40) | 1.40 | 0.8 | 1.2 | 247 | 339 | 91 | 85 | 0.72 |
| C1 (m, 62) | 1.20 | 1.1 | 2.3 | 264 | 328 | 62 | 54 | 0.91 |
| D1 (m, 58) | 0.99 | 1.0 | 1.6 | 285 | 346 | 54 | 50 | 0.17??? |
| Dynamics - 5 point Measurements - day X + 9 | | | | | | | | |
| A1 (m, 34) | 0.7 | | | | | | | |
| B1 (m, 40) | 1.0 | | | | | | | |
| C1 (m, 62) | 0.90 | | | | | | | |
| D1 (m, 58) | 0.82 | | | | | | | |
| Dynamics - 6 point Measurements - day X + 11 | | | | | | | | |
| A1 (m, 34) | 0.63 | | | | | | | |
| B1 (m, 40) | 0.80 | | | | | | | |
| C1 (m, 62) | 0.72 | | | | | | | |
| D1 (m, 58) | 0.54 | | | | | | | |
| Dynamics - 7 point Measurements - day X + 14 | | | | | | | | |
| A1 (m, 34) | 0.69 | 1.4 | 2.8 | 265 | 384 | 52 | 41 | 0.65 |
| B1 (m, 40) | 0.82 | 1.2 | 2.1 | 253 | 375 | 58 | 50 | 0.59 |
| C1 (m, 62) | 0.64 | 1.4 | 2.2 | 285 | 389 | 45 | 40 | 0.71 |
| D1 (m, 58) | 0.53 | 2.1 | 1.7 | 279 | 392 | 42 | 35 | 0.64 |

Experimental group 2

| Designation, sex, age | Antioxidant system (blood) | | | | | Enzymes (blood) | | Triglycerides (blood) [mmoi/l] |
|---|---|---|---|---|---|---|---|---|
| | MDA (urine) [nM/ml] | Vit. A [mcg/ml] | Vit. E [mcg/ml] | Urate [$_{MK}$M] | SH-gr. [$_{MK}$M] | ALT [nmol (sec.l)] | AST [nmol (sec.l)] | |
| Initial level Start of measurements - day X | | | | | | | | |
| A2 (m, 25) | 0.51 | 2.2 | 3.1 | 280 | 384 | 50 | 43 | 0.40 |
| B2 (f, 22) | 0.44 | 2.0 | 3.6 | 286 | 392 | 56 | 40 | 0.35 |
| C2 (m, 40) | 1.51 | 0.4 | 0.5 | 198 | 160 | 205 | 187 | 1.98 |
| D2 (f, 54) | 0.70 | 1.7 | 2.4 | 275 | 319 | 46 | 37 | 0.57 |
| E2 (m, 66) | 0.66 | 1.9 | 2.7 | 279 | 361 | 65 | 59 | 0.89 |
| F2 (m, 42) | 0.56 | 1.9 | 3.0 | 290 | 374 | 52 | 45 | 0.54 |
| G2 (m, 47) | 0.50 | 2.0 | 3.6 | 301 | 395 | 43 | 40 | 0.52 |
| Dynamics - 2 point Measurements - day X + 2 | | | | | | | | |
| A2 (m, 25) | 0.43 | | | | | | | |
| B2 (f, 22) | 0.45 | | | | | | | |
| C2 (m, 40) | 0.99 | | | | | | | |
| D2 (f, 54) | 0.67 | | | | | | | |
| E2 (m, 66) | 0.62 | | | | | | | |
| F2 (m, 42) | 0.45 | | | | | | | |
| G2 (m, 47) | 0.47 | | | | | | | |

-continued

Experimental group 2

| Designation, sex, age | Antioxidant system (blood) | | | | | Enzymes (blood) | | Triglycerides (blood) [mmoi/l] |
|---|---|---|---|---|---|---|---|---|
| | MDA (urine) [nM/ml] | Vit. A [mcg/ml] | Vit. E [mcg/ml] | Urate [$_{MK}$M] | SH-gr. [$_{MK}$M] | ALT [nmol (sec.l)] | AST [nmol (sec.l)] | |
| Dynamics - 3 point Measurements - day X + 4 | | | | | | | | |
| A2 (m, 25) | 0.58 | | | | | | | |
| B2 (f, 22) | 0.51 | | | | | | | |
| C2 (m, 40) | 0.88 | | | | | | | |
| D2 (f, 54) | 0.53 | | | | | | | |
| E2 (m, 66) | 0.60 | | | | | | | |
| F2 (m, 42) | 0.58 | | | | | | | |
| G2 (m, 47) | 0.42 | | | | | | | |
| Dynamics - 4 point Measurements - day X + 7 | | | | | | | | |
| A2 (m, 25) | 0.42 | 2.3 | 3.8 | 295 | 380 | 46 | 41 | 0.43 |
| B2 (f, 22) | 0.38 | 2.7 | 3.2 | 280 | 389 | 50 | 37 | 0.41 |
| C2 (m, 40) | 0.89 | 0.6 | 1.0 | 208 | 197 | 190 | 172 | 1.73 |
| D2 (f, 54) | 0.56 | 1.6 | 2.4 | 279 | 354 | 39 | 30 | 0.42 |
| E2 (m, 66) | 0.55 | 1.9 | 2.6 | 268 | 378 | 61 | 48 | 0.80 |
| F2 (m, 42) | 0.43 | 2.2 | 3.3 | 267 | 389 | 50 | 46 | 0.59 |
| G2 (m, 47) | 0.49 | 2.8 | 3.1 | 311 | 383 | 37 | 31 | 0.44 |
| Dynamics - 5 point Measurements - day X + 9 | | | | | | | | |
| A2 (m, 25) | 0.67 | | | | | | | |
| B2 (f, 22) | 0.54 | | | | | | | |
| C2 (m, 40) | 1.87 | | | | | | | |
| D2 (f, 54) | 0.92 | | | | | | | |
| E2 (m, 66) | 0.98 | | | | | | | |
| F2 (m, 42) | 0.76 | | | | | | | |
| G2 (m, 47) | 0.83 | | | | | | | |
| Dynamics - 6 point Measurements - day X + 11 | | | | | | | | |
| A2 (m, 25) | 0.87 | | | | | | | |
| B2 (f, 22) | 1.00 | | | | | | | |
| C2 (m, 40) | 2.43 | | | | | | | |
| D2 (f, 54) | 0.82 | | | | | | | |
| E2 (m, 66) | 0.98 | | | | | | | |
| F2 (m, 42) | 1.41 | | | | | | | |
| G2 (m, 47) | 0.85 | | | | | | | |
| Dynamics - 7 point Measurements - day X + 14 | | | | | | | | |
| A2 (m, 25) | 0.82 | 1.1 | 2.9 | 215 | 356 | 96 | 88 | 0.72 |
| B2 (f, 22) | 1.07 | 2.1 | 2.6 | 261 | — | 80 | 76 | 0.67 |
| C2 (m, 40) | 2.16 | 0.4 | 1.5 | 149 | 179 | 239 | 217 | 2.08 |
| D2 (f, 54) | 0.79 | 1.2 | 1.9 | 228 | 347 | 79 | 55 | 0.62 |
| E2 (m, 66) | 1.12 | 1.6 | 1.8 | 251 | 354 | 104 | 89 | 1.43 |
| F2 (m, 42) | 0.98 | 1.4 | 2.5 | 247 | 376 | 77 | 68 | 0.79 |
| G2 (m, 47) | 0.99 | 2.0 | 2.1 | 275 | 363 | 89 | 78 | 0.68 |

The invention claimed is:

1. A method for treating a subject for acute alcohol intoxication comprising (a) providing a preparation comprising vicinal dithioglycol of general chemical formula (1):

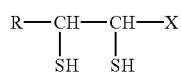 (I)

where R, R$^1$ are selected independently from groups: (—H) or (—COOH) or (—SO$_3$H) or (—OH) or (—CH$_2$—COOH) or (—CH$_2$—SO$_3$H) or (—CH$_2$—O—CH$_2$—SO$_3$H), or a salt of said vicinal dithioglycol comprising (—OH) or (—COOH)) or (—SO$_3$H); and (b) administering the preparation to the subject by peroral or transdermal administration.

2. The method according to claim 1, wherein the preparation comprises a carrier in an amount of up to 99.9999 wt. % of the total weight of the preparation.

3. The method according to claim 1, wherein the preparation is a food additive and the vicinal dithioglycol is an active ingredient of the food additive.

4. A method according to claim 1 for treating acute alcohol intoxication in a patient comprising administering by peroral administration an effective amount of a vicinal dithioglycol of formula (1) to the patient.

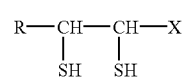 (I)

5. A method as claimed in claim 4, comprising administering the vicinal dithioglycol of general formula (1) to the patient in an effective amount to alleviate the effects of a hangover.

6. The method according to claim 1, wherein R, $R^1$ are selected independently from groups: (—H) or (—COOH) or (—$SO_3H$) or (—OH) or (—$CH_2$—COOH) or (—$CH_2$—O—$CH_2$—$SO_3H$).

7. The method according to claim 1, wherein R, $R^1$ are selected independently from groups: (—H) or (—COOH) or (—OH).

8. A method for treating a subject for acute alcohol intoxication comprising (a) providing a preparation comprising vicinal dithioglycol of general chemical formula (1):

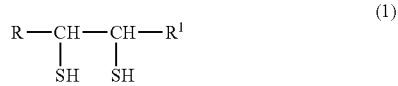

(1)

where R, $R^1$ are selected independently from groups: (—H) or (—COOH) or (—$SO_3H$) or (—OH) or (—$CH_2$—COOH) or (—$CH_2$—$SO_3H$) or (—$CH_2$—O—$CH_2$—$SO_3H$), or a salt of said vicinal dithioglycol comprising (—OH) or (—COOH)) or (—$SO_3H$); and (b) administering the preparation to the subject by peroral or transdermal administration.

9. The method according to claim 8, wherein the preparation comprises a carrier in an amount of up to 99.9999 wt.% of the total weight of the preparation.

10. The method according to claim 8, wherein the preparation is a food additive and the vicinal dithioglycol is an active ingredient of the food additive.

11. The method according to claim 8, wherein R, $R^1$ are selected independently from groups: (—H) or (—COOH) or (—$SO_3H$) or (—OH) or (—$CH_2$—COOH) or (—$CH_2$—O—$CH_2$—$SO_3H$).

* * * * *